US008110188B2

(12) United States Patent
Garzon et al.

(10) Patent No.: US 8,110,188 B2
(45) Date of Patent: Feb. 7, 2012

(54) COMPOSITIONS FOR PREVENTION AND TREATMENT OF INFECTIONS CAUSED BY COCCIDIA IN CHICKENS

(75) Inventors: Jose Andres Morales Garzon, Puebla (MX); Eduardo Lucio Decanini, Puebla (MX)

(73) Assignee: Investigacion Aplicada, S.A. de C.V., Mexico City (MX)

( * ) Notice: Subject to any disclaimer, the term of this patent is extended or adjusted under 35 U.S.C. 154(b) by 154 days.

(21) Appl. No.: 11/241,139

(22) Filed: Sep. 30, 2005

(65) Prior Publication Data

US 2006/0024294 A1 Feb. 2, 2006

Related U.S. Application Data

(63) Continuation-in-part of application No. 10/803,609, filed on Mar. 18, 2004, now abandoned.

(30) Foreign Application Priority Data

Mar. 18, 2003 (MX) ...................... PA/a/2003/003959

(51) Int. Cl.
*A61K 39/395* (2006.01)
*A61K 39/012* (2006.01)
*A61K 39/00* (2006.01)
*A61K 39/42* (2006.01)
*A61K 45/00* (2006.01)

(52) U.S. Cl. ................ 424/130.1; 424/271.1; 424/178.1; 424/267.1; 424/159.1; 424/151.1; 424/157.1; 424/278.1

(58) Field of Classification Search ................ 424/130.1, 424/271.1, 178.1, 267.1, 159.1, 151.1, 157.1
See application file for complete search history.

(56) References Cited

U.S. PATENT DOCUMENTS

| 5,311,841 | A | | 5/1994 | Thaxton |
| 5,753,228 | A | | 5/1998 | Sterling et al. |
| 5,807,551 | A | * | 9/1998 | Reynolds .................... 424/159.1 |
| 5,846,805 | A | | 12/1998 | Collins et al. |
| 6,217,865 | B1 | | 4/2001 | Hunchar |
| 6,998,126 | B2 | * | 2/2006 | Davelaar .................... 424/267.1 |
| 2004/0018215 | A1 | * | 1/2004 | Ellison ........................ 424/269.1 |
| 2006/0057150 | A1 | * | 3/2006 | Kodama et al. ............. 424/184.1 |

FOREIGN PATENT DOCUMENTS

WO          01/59077 A1       8/2001

OTHER PUBLICATIONS

Wallach et al (Passive immunization of chickens against *Eimeria maxima* infection with a monoclonal antibody developed against a gametocyte antigen, Infection and Immunity, 1990; 58(2): 557-62).*
Dalloul et al (Poultry coccidiosois: recent advancements in control measures and vaccine development, Expert Rev. Vaccines, 2006; 5(1): 143-163).*
Smith et al (Maternal transfer of antibodies induced by infection with *Eimeria maxima* partially protects chickens against challenge with *Eimeria tenella*, Parasitology, 1994; 109: 551-7).*
Larsson, A. et al., Chicken Antibodies: A Tool to Avoid False Positive Results by Rheumatoid Factor in Latex Fixation Tests, Journal of Immunological Methods, 1988, pp. 205-208, vol. 108, Elsevier Science Publishers B.V.
Larsson, A. et al., Chicken Antibodies: A Tool to Avoid Interference by Complement Activation in ELISA, Journal of Immunological Methods, 1992, pp. 79-83, vol. 156. Elsevier Science Publishers B.V.
Larsson, A. et al., Chicken Antibodies: Taking Advantage of Evolution—A Review, Poultry Science, 1993, pp. 1807-1812, vol. 72.
Marquardt, R., Antibody-loaded Eggs for Piglets; Prevention of Mortality of Baby Pigs from Diarrhea, Proceedings of the Second International Symposium on Egg Nutrition and Newly Emerging Ovo-Technologies, 1998, p. 39, Alberta, Canada.
Schade. R. et al., The Production of Avian (Egg Yolk) Antibodies: IgY, ATLA., 1996, pp. 925-934, vol. 24.
Tizard, I.R., Principios Generales de Vacunacion y Vacunas, 1998, pp. 295-313, Immunologia Veterinaria, 5aEd., McGraw-Hill (English translation is: Vaccination and Vaccines, 1996, pp. 265-284, Veterinary Immunology, 5th Ed., W. B. Saunders Company).
Yokoyama, H. et al., A Two-Step Procedure for Purification of Hen Egg Yolk Immunoglobulin G: Utilization of Hydroxypropylmethylcellulose Phthalate and Synthetic Affinity Ligand Gel (Avid AL), Poultry Science, 1993, pp. 275-281, vol. 72.
Hatta, H. et al., Passive Immunization Against Dental Plaque Formation in Humans: Effect of a Mouth Rinse Containing Egg Yolk Antibodies (IgY) Specific to *Streptococcus mutans*, Caries Research, 1997, pp. 268-274, vol. 31, S. Karger AG.
Altschuch, D. et al., Determination of IgG and IgM Levels in Serum by Rocket Immunoelectrophoresis Using Yolk Antibodies from Immunized Chickens, Journal of Immunological Methods, 1984, pp. 1-7, vol. 69, Elsevier Science Publishers B.V.
Converse, K. et al., Screening for Potential Human Pathogens in Fecal Material Deposited by Resident Canada Geese on Areas of Public Utility, National Wildlife Health Center, 1999, www.nwhc.usgs.gov/pub_metadata/canada_geese.html.
Diaz, R. et al., Algunos Aspectos de la Coccidiosis Aviar en la Zona de Coatzacoalcos, Veracruz, Mexico (Some Aspects on Poultry Coccidiosis in the Area of Coatzacoalcos in the State of Veracruz in Mexico), Vet. Mex., 2002, pp. 63-71, vol. 33, No. 1, edigraphic.com.
Friend, M. et al., Intestinal Coccidiosis, Field Manual of Wildlife Diseases: Birds, Chapter 26, pp. 207-214.
Ikemori, Y. et al., Protection of Neonatal Calves Against Fatal Enteric Colibacillosis by Administration of Egg Yolk Powder from Hens Immunized with K99-piliated Enterotoxigenic *Escherichia coli*, American Journal of Veterinary Residency, 1992, pp. 2005-2008, vol. 53, No. 11.

(Continued)

*Primary Examiner* — Vanessa L Ford
*Assistant Examiner* — Lakia Tongue
(74) *Attorney, Agent, or Firm* — Panitch Schwarze Belisario & Nadel LLP

(57) ABSTRACT

The invention refers to anticoccidial compositions consisting mainly of yolk immunoglobulins derived from eggs of hens immunized with one or more *Eimeria* species. The invention refers also to the use of said anticoccidial compositions for prevention or treatment of coccidiosis. The administration of immunoglobulins, both in liquid as well as in powder or pellet presentation, decreases mortality, lesions, oocysts counts and increases weight gain of receiving animals.

10 Claims, No Drawings

OTHER PUBLICATIONS

Kashala, O. et al., Safety, Tolerability and Immunogenicity of New Formulations of the *Plasmodium falciparum* Malaria Peptide Vaccine SPf66 Combined with the Immunological Adjuvant QS-21, Vaccine, 2002, pp. 2263-2277, vol. 20, Elsevier Science, Ltd.

Kuroki, M. et al., Passive Protection Against Bovine Rotavirus in Calves by Specific Immunoglobulins from Chicken Egg Yolk, Archives of Virology, 1994, pp. 143-148, vol. 138, Springer-Verlag, Austria.

* cited by examiner

COMPOSITIONS FOR PREVENTION AND TREATMENT OF INFECTIONS CAUSED BY COCCIDIA IN CHICKENS

CROSS REFERENCE TO RELATED APPLICATIONS

This non-provisional application is a continuation-in-part of prior non-provisional application Ser. No. 10/803,609 filed Mar. 18, 2004 now abandoned, which claimed priority to Mexican patent application PA/a/2003/003959, filed Mar. 18, 2003.

FIELD OF THE INVENTION

The present invention consists in offering new compositions for treatment and prevention of infections caused by *Eimeria* parasites in broiler chickens based on oral administration of such compositions.

BACKGROUND OF THE INVENTION

There are two ways of protecting animals against infectious agents: they can be exposed to antigens derived from an infectious agent to stimulate a protective immune reaction or they can receive a preformed antibody obtained from an immunized subject.

The first way is conducted through different types of vaccines: freeze-dried live viruses or bacteria, through dead viruses or bacteria in oily emulsions; and recently through the creation of cloned and recombinant vaccines. Each of them presents advantages and drawbacks with regard to protection, immune response and protection duration. Besides, in some cases, the first general approach may lead to undesirable complications in the host due to the vaccination (Tizard, I. R. 1998)

The second form of protection, also called passive immunity, includes the transference of specific antibodies against infectious agents into A susceptible subject.

Traditionally, at the research level, antibodies are mainly obtained from mammals and less frequently from birds. The types of antibodies obtained are monoclonal and polyclonal antibodies in mammals, and polyclonal antibodies in birds (Larsson, et al. 1993).

In the case of birds, the chicken is the only species from which antibodies are obtained in a most accessible and highly defined form. The main serum antibody present in the chicken is IgG, even though IgG is transported to the egg in a similar way to the transfer of mammal IgG through the placenta.

In the egg, IgG is found in higher concentrations in the yolk than in the white; it is even found in larger quantities in the yolk than in the hen serum (Larsson, et al. 1993).

To have an idea of the quantity of antibodies made in the hen, we must take into account that an egg-laying hen produces approximately 5 to 6 eggs per week with a yolk volume of about 15 ml. Thus, in a week, a hen produces antibodies in yolk equivalent to 90-100 ml of serum or 180-200 ml of whole blood. This is to be compared with the 20 ml of whole blood given per week by an immunized rabbit. Obviously if we use animals such as horses or cows, the quantity of serum and antibodies is larger than in the egg but it is more expensive and more painful for the animals.

Egg yolk antibodies (immunoglobulins-Ig's) have been employed as tools for diagnosis and therapy (Schmidt, et al. 1989). Thus, taking advantage of its phylogenetic difference with mammal immunoglobulins, the Ig's have presented several advantages when used in immune diagnosis. For example, yolk Ig's have been used to detect several viruses through ELISA, immunodiffusion, and immunofluorescence. Because of their low isoelectric point, compared to human IgG, they are employed in electrophoresis assays for the quantification of immunoglobulins in the serum of several animals (Altschuh, D. 1984, Larsson, et g. 1988, Larsson, et al. 1992, Larsson, et al. 1993, Schade, R. 1996). With regard to their therapeutic application, the Ig's have been used as immunotherapy in some scientific fields. For example, the administration of egg yolk immunoglobulins orally has prevented rotavirus infections in mice, bovines, and pigs, among others (Ikemori, et al 1992, Kuroki, et al 1994, Marquardt, et al 1998). Moreover, they have been used as antivenins against viper and scorpions that can be injected to neutralize the toxins without the risk of anaphylactic reactions, such as those reactions commonly caused by antivenins obtained from immunized horses (Larsson, et al. 1993). A further application was to prevent caries caused by *Streptococcus mutans* in humans (Hata, H. et al 1984).

In the past, several methods have been used in attempts to control coccidiosis including the use of chemical drugs and vaccines including live and recombinant vaccines. However, there are problems with existing coccidiosis vaccines, such as reduced efficacy, cross-infection with other parasites (e.g., *Clostridium* sp.) and poor bird performance. Monoclonal and recombinant antibodies are still under experimentation. Vaccines would have some positive impact in preventing infections but they are not suitable for reducing ongoing infections.

At present the use of antibodies obtained from either mammals or birds for treatment or prevention of coccidia infections caused by *Eimeria* species has not been reported. Reynolds, in U.S. Pat. No. 5,807,551, describes a method for inducing long-term passive immunity in birds but research was limited to Newcastle disease virus and infectious bursal disease virus. Sterling et al., in U.S. Pat. No. 5,753,228, discloses a method for treating infestions caused by *Cryptosporidium parvum* in mammals. Thus, there is a need for efficacious coccidiosis and coccidiosis control methods.

SUMMARY OF THE INVENTION

An object of at least one of the preferred embodiments disclosed herein is to offer prevention and treatment methods of coccidia infections in birds with the use of compositions suitable for the oral administration through drinking water or mixed with food or through the use of anticoccidial food.

The invention also provides new compositions from anticoccidial immunoglobulins obtained from the egg of hyperimmunized hens, and more specific from the yolk of such eggs. The new compositions consist of one or more anticoccidial immunoglobulins.

The invention also prevents weight loss to the animals treated with a composition of anticoccidial immunoglobulins specifically directed against *Eimeria* type coccidia parasites.

Moreover, within the scope of the present invention, the use of egg yolk anticoccidial immunoglobulin compositions against parasites is claimed to eliminate or substantially reduce the symptoms, mortality and ill transmission in the treated animals.

Finally, the invention discloses a process to prepare a composition or a food containing such immunoglobulins specifically directed against coccidia parasites of chicken obtained from yolk of eggs produced by hyperimmunized hens.

Through the present invention, in the case of animals, the quantity of oocysts of protozoans in the digestive tract decreases, and the productive parameters of the animals improve.

DETAILED DESCRIPTION OF THE INVENTION

The detailed characteristics of the novel invention disclosed herein are clearly shown in the following description.

The present invention is based on the fact that the immunoglobulins extracted from the aqueous phase of the yolk of eggs produced by hyperimmunized hens offer protection against parasites illnesses or infection.

To obtain the immunoglobulins (Igs) specifically directed against animal parasites, it is necessary to have a vaccination schedule in a flock of SPF (Specific Pathogens Free) birds.

The vaccination schedule can include the administration, orally, subcutaneously or through any other way, of an effective amount of the antigen to reduce infection or its symptoms. The effective amount is calculated to induce an effective response without causing infection.

The parasite could be administered live or dead. Ways to kill parasites are through chemical or physical methods known to those skilled in the art.

The immunization program includes inoculations of each particular coccidia-causing parasites in order to development specific immune response against such parasites.

In the preferred embodiments of the invention the antigen administered could be the parasite in any stage of its lifecycle, including oocyst, sporozoites, merozoites or whole parasites from the family of *Eimerias* consisting of *E. tenella, E. acervulina, E. maxima, E. necatrix, E. brunetti, E. mitis, E. praecox* or *E. hagani*.

Through extensive experimentation we have found that the use of a mix of two or more species such as *E. tenella, E. acervulina, E. maxima, E. necatrix, E. brunetti, E. mitis, E. praecox* or *E. hagani* provides better results than using only one particular species. The main reason is that each *Eimeria* species has a different mechanism of action due to little differences in structure between them.

To obtain the anticoccidial immunoglobulins, live or dead parasites are administered orally in an antigen suspension combined with parenteral administration of an oily or semi-oily vehicle or within vehicle of any other type in such a way as to ensure an immune response in the hen.

The parasites administered are selected from the following *Eimeria*' species: *E. acervulina, E. maxima, E. tenella, E. necatrix, E. brunetti, E. mitis, E. praecox, E. hagani* or combination of two or more species.

The recommended parasites dose is 4,000 to 20,000 parasites in any stage of its lifecycle contained in 0.3-0.8 ml of the antigen solution used for immunized laying hens in the growing stage at 8, 12 and 16 weeks of age. A booster vaccination could be carried out every 3-8 weeks.

Once the eggs from the immunized laying hens show anticoccidial immunoglobulins, measured by microneutralization test (MNT), the eggs are collected.

The yolk from the eggs containing anti-*Eimeria* immunoglobulins is collected, separated and purified from the white by well known methods by a person skilled in the art and diluted 1:2-1:8 with a 0.005-0.01% sodium azide solution or any other preservative solution to obtain anticoccidial composition. The purification step consists optionally of lipoprotein removal.

It is preferred to use anticoccidial composition with titers of 1:16-1:128.

The anti-*Eimeria* immunoglobulins from the yolk of eggs produced by an immunized hen contain one or more specific anti-*Eimeria* immunoglobulins, preferably 0-35% of *E. acervulina* specific immunoglobulin, 0-2-% of *E. brunette* specific immunoglobulin, 0-20% of *E. maxima* specific immunoglobulin and 25-90% of *E. tenella* specific immunoglobulin.

The anti-*Eimeria* immunoglobulins from the yolk of eggs produced by an immunized hen could be obtained by immunization of the hen with an effective amount of a mix of two or more antigens of the different *Eimeria* species.

In another preferred embodiment of the invention the anti-*Eimeria* composition is prepared by obtaining each one of the specific anti-*Eimeria* immunoglobulins from the yolk of eggs produced by an immunized hen with each one of the *Eimeria* species and mixing them in correct quantities. The anticoccidial composition has the following specification: Anti-*Eimerias* immunoglobulins yolk 15-30%, water 70-85% and preservative 0.001-0.03%.

The liquid composition is suitable for both coccidian infection treatment and therapeutic methods. Liquid anticoccidial composition could be administered in broiler birds from 2 weeks of age to eight weeks as preventive method at a dose of 0.5-2 ml per bird per oral route daily during 1-2 weeks and as therapeutic method at a rate of 2-4 ml per bird by oral route during 2-3 days.

For coccidia infection prevention, it was found through several experiments that good results are also encountered if the anticoccidial immunoglobulins composition is added to chickens' food.

In order to add to the chickens' food, the anti-*Eimeria* composition is dehydrated through the Spray Dried method.

The powder anticoccidial composition is mixed with any suitable food, by any well known methods of food producing, at a rate of 0.1-1 kg of powder anticoccidial yolk composition per ton of chickens' food. Bird food with anticoccidial composition could also be formulated in pellets.

Anticoccidial composition with bird food could be administered during the whole growing period of broiler chickens to prevent infections caused by *Eimeria* parasites.

As could be inferred from the present invention disclosure, specific *Eimeria* specie or species to produce the anticoccidial composition could be selected depending on that specific species found in the geographical area where the animals are growing.

The quality control tests of anticoccidial composition include:

1.—Sterility test to check if the product is free from contamination by bacteria, fungi and yeast according to the Code of Federal Regulations of the United States of America.

2.—Antibody quantification. ELISA techniques or any other method like Microneutralization test (MNT) in chicken cell cultures were used to detect specific immunoglobulins for different coccidia species.

The yolk and serum titers by MNT were expressed as the reciprocal of the highest dilution in which citopathic effect was observed, the Igs titer obtained must be 1:4-1:128.

3.—Innocuous assay in order to detect physiologic alterations or injury in the immunoglobulins recipient.

Hereinafter tests are presented as non-limiting examples showing the use of immunoglobulins against coccidian in broiler chicken as objects of the present invention.

Example 1

A liquid anticoccidial composition was prepared according to the detailed invention having 17% of Anti-*Eimeria* immunoglobulins with a titer of 1:8 to *E. tenella*, 0.001% of sodium azide and water. 40 broiler chickens 3 weeks-old were fed without any anticoccidial drugs during ten day and then 5 groups were formed. Group 1 remained as Control Group without anticoccidial composition treatment.

Group 2, 3, 4 and 5 received respectively 0.5, 1, 2 and 4 ml of liquid anticoccidial composition by oral route, one dose at day 1 and a second dose 8 days later. When birds were 31 days old, they were challenged with 200,000 sporulated oocysts of *E. tenella* by oral route. The animals were sacrificed 7 days after the challenge to determine lesions according to well known Johnson and Reid method, based on severity of lesion in a scale ranged from 0 to 4, where 0 mean no lesion and +4 severe lesions, and caecal weight. It is well known that chickens with *E. tenella* infection increase their caecal weights because there is an inflammatory process resulting in a swelling of the caecal wall. The results are shown in Table 1. It can be observed that all groups with treatment maintain lower caecal weight compared to the caecal weight of the control group. The lesions of the treated groups were lower than in the control group.

TABLE 1

| Group | No of birds | Liquid Immunoglobulins composition Volume ml | Caecal weight g | Lesion Score Johnson- Reid Scale |
|---|---|---|---|---|
| 1 | 8 | 0.0 | 24.3 | +4 |
| 2 | 8 | 0.5 | 22.9 | +2 |
| 3 | 8 | 1.0 | 21.0 | +2 |
| 4 | 8 | 2.0 | 15.0 | +2 |
| 5 | 8 | 4.0 | 13.6 | +3 |

Example 2

Two groups of 25 broiler birds were formed: Group 1 received 1 ml of liquid anticoccidial composition, prepared as described in Example 1, on daily basis through drinking water during two weeks. The control group did not receive any treatment. After two weeks of treatment, both groups were challenged with 150,000 sporulated oocysts of *E. tenella* per ml by oral route.

All the animals were sacrificed 7 days later and the caecal lesions were qualified according to Johnson and Reid method. Mortality was also recorded. Results are given in Table 2. In the treated group mortality, caecal weight and lesion score according to Johnson-Reid scale were lower than in the control group.

TABLE 2

| Group | No of birds | Mortality % | Caecal weight (g) | Lesion Score Johnson- Reid Scale |
|---|---|---|---|---|
| 1 | 25 | 55 | 16.2 | +2 |
| Control | 25 | 83.3 | 35.0 | +4 |

Example 3

Three groups of 30 one-week old broiler birds were formed. The first group received 2 ml of liquid immunoglobulins composition prepared as described in Example 1 against coccidia, consisting of 17% of anti-*Eimeria* immunoglobulins with titer of 1:32 obtained through hen immunization with 800 oocysts from *E. acervulina*, 450 oocysts from *E. brunetti*, 450 oocysts from E. maxima and 1100 oocysts from *E. tenella*, 0.001% of sodium azide and water, through drinking water on a daily basis during 14 days and they were fed with food without anticoccidial drugs. The second group was fed with a commercial polyether anticoccidial drug and the last group remained as a control group.

After the treatment period with liquid immunoglobulins composition, all groups were challenged by oral route with 200,000 sporulated oocysts per ml of a mixture of *E. acervulina* (72.5%), *E. brunetti* (12.5%), *E. maxima* (12.5%) and *E. tenella* (2.5%). The parameters to evaluate were: weight gain, oocysts counts in caecal content and conversion index (CI), calculated as the ratio of weight feed to weight gain. Results are presented in Table 3. The group treated with the anticoccidial composition showed 68.5% weight gain compared to the control group and 44% weight gain compared to the group treated with the commercial drug. With regard to oocysts recovery, in the group treated with the anticoccidial composition there was no recovery while in the group that received food with anticoccidial drug, the average count was 192,000 and 288,000 oocysts in the control group. The better conversion index (CI=2.23) was observed in the treated group compared with group 2 (CI=3.22) and group 3 (CI=3.90).

TABLE 3

| Group | No of Birds | Final weight gain (g) | Oocysts in caeca contents | Oocysts in intestinal contents | Conversion Index |
|---|---|---|---|---|---|
| 1 | 30 | 337.0 | 0.0 | 0.0 | 2.33 |
| 2 | 30 | 234.0 | 288,000 | 192,000 | 3.22 |
| 3 | 30 | 200 | 576,000 | 288,000 | 3.90 |

Example 4

75 two-weeks old broiler chickens were divided in two groups of 30 and one group of 15 birds. The groups were identified as Group A, B and C. During the whole experiment the birds consumed food without anticoccidial drug. Group A received 2 ml of liquid immunoglobulins composition mentioned in Example 3 on a daily basis by drinking water during 4 weeks. After 4 weeks the bird weights were recorded. Group A and B were challenged with 150,000 sporulated oocysts of *E. tenella* per ml by oral route. Group B received food with anticoccidial drug after the challenge. Group C remained as a control group. One week later all birds were sacrificed and were scored the following data weight gain and lesions scored by Johnson and Reid method. Results are shown on Table 4 where it can be observed that there is a better weight gain (208.2 g) in Group A treated with immunoglobulins composition compared with Group B (46.7 g) and the control group (6.7 g). Also Group A showed less lesions (scale +2) than Group B (score+4) and the control group (score+4).

TABLE 4

| Group | No of Birds | Weight (g) | | | Lesion Score Johnson- Reid Scale |
|---|---|---|---|---|---|
| | | Before Challenge | After challenge | Difference | |
| A | 15 | 636.6 | 844.8 | 208.2 | +2 |
| B | 15 | 626.6 | 673.3 | 46.7 | +4 |
| C | 15 | 613.3 | 620.0 | 6.7 | +4 |

Example 5

Three groups of 10 3-week old age broiler chickens were formed and maintained on wire cages. All birds were challenged with 100,000 sporulated oocysts of *E. tenella* per ml by oral route. After 4-5 days, Group A of 10 birds were treated with 2 ml of liquid immunoglobulins composition of Example 3 on a daily basis during 2 days; Group B of 10 birds were treated with a commercial anticoccidial drug according to manufacturer instructions (1 ml of anticoccidial drug per 1000 ml of water on daily basis during 2 days). Group C remained as the Control Group without treatment.

All birds were fed with a food without anticoccidial drug or growing additive during whole experiment.

Four days later all birds were weighted and sacrificed, in order to establish weight gain and lesions on caecal according to Johnson and Reid scale.

Results are showing on Table 5. Group A showed a little better weight gain than birds treated with anticoccidial drug but group A treated with liquid immunoglobulins composition showed less lesions (average lesion of 2.1) compared with lesions of anticoccidial drug treated group (3.0 average). The Control Group showed an average score of 3.5 and there was no practical weight gained. In normal conditions birds infected with coccidian lose weight and have high mortality.

TABLE 5

| Group | No of Birds | Average Weight Gain (g) | Average Score lesion |
|---|---|---|---|
| A | 10 | 107.5 | 2.1 |
| B | 10 | 103.9 | 3.0 |
| C | 10 | 5.5 | 3.5 |

Example 6

Five groups of 10 2-week old broiler chickens were formed. Four types of food were manufactured, three of them were in powder presentation containing 200 g of immunoglobulins composition prepared according to Example 3 per ton of food. The three foods contained a titer of immunoglobulins composition of 1:4, 1:64 and 1:128 measured previously by a microneutralization test in kidney chicken cell culture; the last one food was manufactured without immunoglobulins composition and without growth additive.

Group 1, Group 2 and 3 were treated during a week with an anticoccidial food with a titer of 1:4, 1:8 and 1:64 respectively; Groups 4 (Positive Control) and 5 (Negative Control) were fed with a food without anticoccidial drug nor anti-*Eimeria* immunoglobulin yolk composition. A week later all birds except the Negative Control were challenged with 100,000 sporulated oocysts of *E. tenella* by oral route. The feeding schedule was maintained during the whole experiment. One week after the challenge with *E. tenella* all birds were sacrificed and necropsied to score lesions by the Johnson and Reid method. A sample of feaces was taken per group to determine counts of oocysts per weight. Results are shown on Table 6 where it can be observed that animals fed with food with the anticoccidial composition with a titer of 1:4 showed lesions of +3 scale similar to the control group. However, animals fed with anticoccidial food with a titer with 1:64 and 1:128 showed lower score lesion +2 considering only a week of treatment. There could be observed a decrease in count of oocysts per gram of faeces while titer et of immunoglobulins composition was increased.

TABLE 6

| Group | No of birds | Average Score lesion | Count of oocysts per g of faeces |
|---|---|---|---|
| 1 | 10 | 3 | 765,000 |
| 2 | 10 | 2 | 615,000 |
| 3 | 10 | 2 | 407,000 |
| 4 | 10 | 3.5 | 805,000 |
| 5 | 10 | 0.5 | 0 |

Example 7

Two groups of 25 two-weeks old broiler chickens were formed. The groups were identified as Group A and B. During three weeks the birds consumed food without anticoccidial drug. During the next week, Group A was fed with food with 500 g of powder immunoglobulins composition obtained by spray dried from composition of Example 3, and the same composition was used to form pelleted food with same rate of immunoglobulins per food and it was administered to Group B. After one week that the bird were fed with anticoccidial food, Group A and B were challenged with 100,000 sporulated oocysts of *E. tenella* by oral route. Both groups received the same food as previous week with anticoccidial immunoglobulins after the challenge. One week after all birds were sacrificed and were scored for: weight gain and lesions scored by Johnson and Reid method. Results are showed on Table 7 where similar results in weight gain and lesions can be observed.

TABLE 7

| Group | No of Birds | Weight gain(g) | Lesion Score Johnson-Reid Scale |
|---|---|---|---|
| A | 25 | 427 | +1.1 |
| B | 25 | 483 | +1.4 |

BIBLIOGRAPHY

Altschuh, D. et al. 1984. Determination of IgG and IgM levels in serum by Rocket Immunoelectrophoresis using yolk antibodies from Immunized chickens. J. Immunolog. Methods. 69:1-7

Hatta, H. et al. 1997. Passive Immunization Against Dental Plaque Formation in Humans: Effect of a Mouth Rinse containing Egg Yolk Antibodies (IgY) Specific to *Streptococcus mutans*. Caries. Res. 31:268-274.

Ikemori, Y. et al. 1992. Protection of neonatal calves against fatal enteric colibacillosis by administration of egg yolk powder from hens immunized with k99-pillated enterotoxigenic *Escherichia coli*. Am. J. Vet. Res. 53:2005-2008.

Kuroki, M. et al 1994. Passive protection against bovine rotavirus in calves by specific immunoglobulins from chicken egg yolk. Arch. Virol. 138: 143-148.

Larsson, A. et al. 1988. Chicken antibodies: a tool to avoid false positive results by rheumatoid factor in latex fixation tests. J. Immunol. Methods. 108:205-208.

Larsson, A. et al. 1992. Chicken antibodies: a tool to avoid interference by complement activation in ELISA. J. Immunol. Methods. 156: 79-83.

Larsson, A. et al. 1993. Chicken antibodies: taking advantage of evolution. A review. Poultry Sci. 72: 1807-1812.

Marquart, R. 1998. Antibody-loaded eggs for piglets: prevention of mortality of baby pigs from diarrhea. Proc. 2$^{nd}$ International Symposium on Egg Nutrition and Newly Emerging Ovo-Technologies. Alberta, Canada.

Schade, R. et al 1996. The production of avian (Egg yolk) antibodies:IgY. Atla. 24:925-934.

Tizard, I. R. 1998. Vacunaciön y vacunas In: Immunologia Veterinaria. 5$^a$ Ed. Mc Graw-Hill. pp 285-305.

Yokoyama, H. et al. A two step procedure for purification of hen yolk immunoglobulin G: Utilization of Hydroxypropylmethylcellulose phtalate and synthetic affinity ligand gel (Avid AL®). Poultry Sci. 72:275-281.1993.

We claim:

1. A composition comprising 0.1-1 kg of concentrated anticoccidial yolk per ton of chicken food, wherein the concentrated anticoccidial yolk comprises immunoglobulins against *E. acervulina, E. maxima, E. tenella* and *E. brunetti* in order to diminish the severity of lesions, decrease the caecal weight and decrease oocyst count in feces of chickens, and wherein the concentrated anticoccidial yolk is obtained from yolks of eggs produced by hens which are immunized with *E. tenella, E. acervulina, E. maxima* and *E. brunetti* to provide immunization against *E. tenella, E. acervulina, E. maxima* and *E. brunetti*.

2. The composition of claim 1, wherein said hens are immunized with a mix comprising 39 parts of *E. tenella*, 29 parts of *E. acervulina*, 16 parts of *E. maxima* and 16 parts of *E. brunetti*.

3. The composition of claim 1, wherein said hens are immunized with oocysts or sporozoites or merozoites of *E. tenella., E. acervulina., E. maxima* and *E. brunetti*.

4. The composition of claim 1, wherein said chickens are broiler chickens.

5. The composition according to claim 1, wherein the anticoccidial yolk comprises immunoglobulins having a neutralizing titer of 1:16-1:128 as measured by a micro-neutralization test.

6. The composition according to claim 1, wherein the composition comprises 0.1-0.5 kg of concentrated anticoccidial yolk per ton of chicken food.

7. The composition according to claim 1, wherein the immunoglobulins are combined in the following percentages:
   25-90% of immunoglobulins against *E. tenella*,
   up to 35% of immunoglobulins against *E. acervulina*,
   up to 20% of immunoglobulins against *E. maxima*, and
   up to 20% of immunoglobulins against *E. brunetti*.

8. The composition according to claim 1, wherein the concentrated anticoccidial yolk is in powder form and is admixed with the chicken food.

9. The composition according to claim 1, wherein the composition is in pellet form.

10. The composition according to claim 1, wherein the concentrated anticoccidial yolk consists essentially of immunoglobulins against *E. tenella, E. acervulina, E. maxima*, and *E. brunetti*.

* * * * *